United States Patent [19]

Kaminski et al.

[11] 4,171,452

[45] Oct. 16, 1979

[54] ANTIBACTERIALLY ACTIVE N-CHLOROAMINO ESTER DERIVATIVES OF ALKYL CARBOXYLATES

[75] Inventors: James J. Kaminski; Nicolae S. Bodor, both of Lawrence, Kans.

[73] Assignee: INTERx Research Corporation, Lawrence, Kans.

[21] Appl. No.: 797,469

[22] Filed: May 16, 1977

Related U.S. Application Data

[62] Division of Ser. No. 632,012, Nov. 14, 1975, Pat. No. 4,036,843.

[51] Int. Cl.$^2$ ............................................. C07C 69/02
[52] U.S. Cl. .................................................. 560/253
[58] Field of Search ........................................ 560/253

[56] References Cited

U.S. PATENT DOCUMENTS 3,998,815  12/1976  Bodor .................................. 560/253

Primary Examiner—Alan L. Rotman
Attorney, Agent, or Firm—Burns, Doane, Swecker & Mathis

[57] ABSTRACT

There is provided, a novel class of compounds exhibiting antibacterial activity and having the formula:

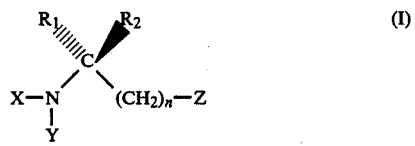

wherein
X and Y each represent a member which may be the same or different selected from the group consisting of H and Cl with the proviso that X and Y cannot represent H simultaneously;
$R_1$ and $R_2$ each represent a member which may be the same or different selected from the group consisting of an n- or branched alkyl group of from 1 to 20 carbon atoms, an aryl group (phenyl, naphthyl, etc.) and

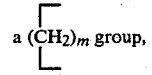

a $(CH_2)_m$ group, wherein m represents an integer of from 2 to 5; n represents an integer of 1 to 8; and Z represents a member selected from the group consisting of an —OOCR$_3$ group, an —OR$_3$ group and an —OCH$_2$OR$_3$ group,
wherein R$_3$ represents a member selected from the group consisting of an n- or branched alkyl group of 1 to 20 carbon atoms, a phenyl group, a naphthyl group, a benzyl group,

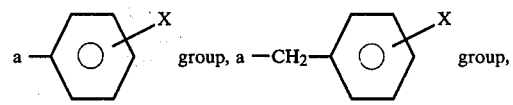

wherein X is a halogen atom (Cl, Br, I),

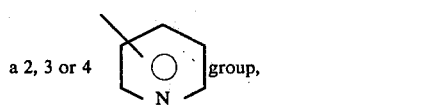

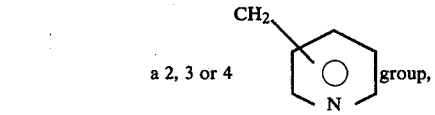

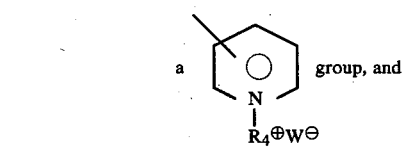

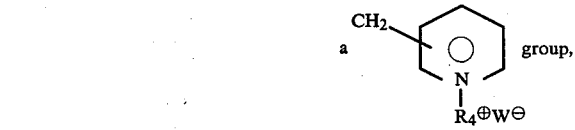

wherein R$_4$ represents a member selected from the group consisting of H, an n- or branched alkyl group, a benzyl group, an O atom, and a —(CH$_2$)$_p$COOH group, wherein p represents an integer of 1 to 4, and wherein W$^\ominus$ represents a non-toxic pharmaceutically acceptable inorganic or organic anion.

18 Claims, No Drawings

ANTIBACTERIALLY ACTIVE N-CHLOROAMINO ESTER DERIVATIVES OF ALKYL CARBOXYLATES

CROSS REFERENCE TO RELATED APPLICATIONS

This application is a divisional application of our earlier co-pending application, Ser. No. 632,012, filed Nov. 14, 1975, now U.S. Pat. No. 4,036,843.

BACKGROUND OF THE INVENTION

1. Field of the Invention

The present invention is directed to a novel class of antibacterial compounds and more specifically, the present invention is directed to a novel class of antibacterial compounds which are termed soft N-chloramino alcohol derivatives as described later. The term "antibacterial" as employed in this application, includes both "antifungal" and "antibacterial" activity.

2. Description of the Prior Art

N-chloramines such as the N-chlorinated naturally occurring amino acids as well as their derivatives are presently known. However, in the main, these compounds have not been isolated, or if isolated, can undergo rapid and often explosive decomposition. Illustrative of such a compound undergoing explosive decomposition upon isolation is methyl N-chlorosarcosinoate. James J. Kaminski, Nicolae Bodor and Takeru Higuchi; *J. Pharm. Sci.*, 64, 0000 (1975).

Similarly, simple chloramines (e.g., chloramine per se) can undergo disproportionation, providing as one by-product $NCl_3$, a well-known toxic material.

Due to the low water solubility and low boiling point of simple chloramines, they simply evaporate too quickly from an aqueous solution, and as such, a sterilizing aqueous solution containing a simple chloramine is characterized by extremely low persistency.

Moreover, the simple chloramines (e.g., $NH_2Cl$, $NHCl_2$) are known to be readily deactivated by denaturing agents (e.g., horse serum), thus quickly diminishing the antibacterial activity of such compounds.

Methyl-α-N,N-dichloroaminoisobutyrate is also known, but only to the extent that it has been used to study the mechanism and kinetics of the dimerization of N,N-dichloro derivatives in strong bases. As such, no known antibacterial utility has been recognized for this compound. See, A. M. Pinchuk, L. N. Markovskii and G. K. Bespalko, *Zh. Org. Khim.*, 7, 2263 (1971) and Julius J. Fuchs, U.S. Pat. No. 3,530,162 (1970).

SUMMARY OF THE INVENTION

Accordingly, it is one object of the present invention to provide a novel class of compounds exhibiting substantial antibacterial and antifungal activity.

It is another object of the present invention to provide a novel class of antibacterial compounds which will exhibit enhanced stability in the "neat" state.

Still, it is another object of the present invention to provide a novel class of antibacterial compounds which will exhibit enhanced stability in the "neat" state, in addition to further exhibiting substantial antibacterial activity over varying pH conditions.

Still further, it is another object of the present invention to provide a novel class of antibacterial compounds which remain stable in the "neat" state, remain active over varying pH conditions and yet fail to be inactivated as antibacterial agents by conventional denaturants, such as blood serum.

Finally, it is the last object of the present invention to provide a novel class of antibacterial compounds as heretofore described which are biodegraded into non-toxic products.

Accordingly, all the above objects of the present invention can be satisfied with a novel class of antibacterial compounds having the formula:

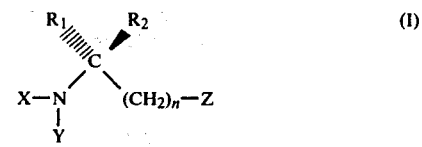

wherein X and Y each represent a member which may be the same or different selected from the group consisting of H and Cl with the proviso that X and Y cannot represent H simultaneously; $R_1$ and $R_2$ each represent a member which may be the same or different selected from the group consisting of an n- or branched alkyl group of from 1 to 20 carbon atoms, an aryl group (phenyl, naphthyl, etc.) and

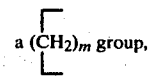

wherein m represents an integer of from 2 to 5; n represents an integer of 1 to 8; and Z represents a member selected from the group consisting of an $-OOCR_3$ group, an $-OR_3$ group and an $O-CH_2-OR_3$ group, wherein $R_3$ represents a member selected from the group consisting of an n- or branched alkyl group of 1 to 20 carbon atoms, a phenyl group, a naphthyl group, a benzyl group,

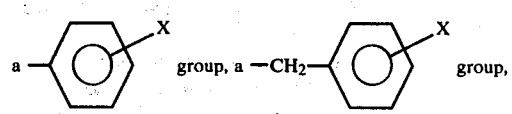

wherein X is a halogen atom (Cl, Br, I),

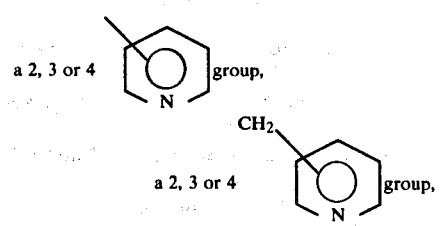

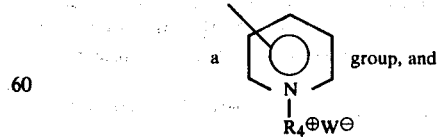

wherein $R_4$ represents a member selected from the group consisting of H, and n- or branched alkyl group, a benzyl group, an O atom, and a $—(CH_2)_p$ COOH group, wherein p represents an integer of 1 to 4, and wherein $W^\ominus$ represents a nontoxic pharmaceutically acceptable inorganic or organic anion.

DETAILED DESCRIPTION OF THE INVENTION

In the above formula, when each of $R_1$, $R_2$ and $R_3$ represent an alkyl group, a carbon range of from 1–5 carbon atoms is preferred. When $R_1$ and $R_2$ represent an aryl group or a

respectively, phenyl is the aryl group of choice and 4 is the integer of choice for m.

The phrase, "nontoxic pharmaceutically acceptable inorganic or organic anion" as used herein generally includes the nontoxic acid addition salts of the compounds of formula (I), formed with nontoxic inorganic or organic acids. For example, the salts include those derived from inorganic acids such as hydrochloric, hydrobromic, sulfuric, phosphoric, nitric and the like; and the salts prepared from organic acids such as acetic, propionic, succinic, stearic, malonic, pamoic, phenylacetic, glutaric, benzoic, toluene-sulfonic, methanesulfonic and the like.

While all the compounds encompassed within the above-described generic formula will satisfy the objectives of the present invention, nevertheless, certain compounds are preferred as set out below:

1. 2-N-Chloroamino-2-methyl-1-propyl acetate.
2. 2-N-Chloroamino-2-methyl-1-propyl propionate.
3. 2-N-Chloroamino-2-methyl-1-propyl butyrate.
4. 2-N-chloroamino-2-methyl-1-propyl isobutyrate.
5. 2-N-Chloroamino-2-methyl-1-propyl valerate.
6. 2-N-Chloroamino-2-methyl-1-propyl isovalerate.
7. 2-N-Chloroamino-2-methyl-1-propyl hexanoate.
8. 2-N-Chloroamino-2-methyl-1-propyl octanoate.
9. 2-N-Chloroamino-2-methyl-1-propyl decanoate.
10. 2-N-Chloroamino-2-methyl-1-propyl dodecanoate.
11. 2-N-Chloroamino-2-methyl-1-propyl tetradecanoate.
12. 2-N-Chloroamino-2-methyl-1-propyl hexadecanoate.
13. 2-N-Chloroamino-2-methyl-1-propyl octadecanoate.
14. 2-N-Chloroamino-2-methyl-1-propyl 2,2-dimethylpropionate.
15. 2-N-Chloroamino-2-methyl-1-propyl benzoate.
16. 2-N-Chloroamino-2-methyl-1-propyl nicotinoate.
17. 2-N-Chloroamino-2-methyl-1-propyl isonicotinoate.
18. 2-N-Chloroamino-2-methyl-1-propyl nicotinate N-oxide.
19. 2-N-Chloroamino-2-methyl-1-propyl isonicotinate N-oxide.
20. 2-N-Chloroamino-2-methyl-1-propyl nicotinate hydrochloride.
21. 2-N-Chloroamino-2-methyl-1-propyl nicotinate methylsulfonate.
22. 2-N-Chloroamino-2-methyl-1-propyl nicotinate methylsulfate.
23. 2-N-Chloroamino-2-methyl-1-propyl isonicotinate hydrochloride.
24. 2-N-Chloroamino-2-methyl-1-propyl isonicotinate methylsulfonate.
25. 2-N-Chloroamino-2-methyl-1-propyl isonicotinate methylsulfate.
26. 2-N,N-Dichloroamino-2-methyl-1-propyl acetate.
27. 2-N,N-Dichloroamino-2-methyl-1-propyl propionate.
28. 2-N,N-Dichloroamino-2-methyl-1-propyl butyrate.
29. 2-N,N-Dichloroamino-2-methyl-1-propyl isobutyrate.
30. 2-N,N-Dichloroamino-2-methyl-1-propyl valerate.
31. 2-N,N-Dichloroamino-2-methyl-1-propyl isovalerate.
32. 2-N,N-Dichloroamino-2-methyl-1-propyl hexanoate.
33. 2-N,N-Dichloroamino-2-methyl-1-propyl octanoate.
34. 2-N,N-Dichloroamino-2-methyl-1-propyl decanoate.
35. 2-N,N-Dichloroamino-2-methyl-1-propyl dodecanoate.
36. 2-N,N-dichloroamino-2-methyl-1-propyl tetradecanoate.
37. 2-N,N-Dichloroamino-2-methyl-1-propyl hexadecanoate.
38. 2-N,N-Dichloroamino-2-methyl-1-propyl octadecanoate.
39. 2-N,N-Dichloroamino-2-methyl-1-propyl 2,2-dimethylpropionate.
40. 2-N,N-Dichloroamino-2-methyl-1-propyl benzoate.
41. 2-N,N-Dichloroamino-2-methyl-1-propyl nicotinoate.
42. 2-N,N-Dichloroamino-2-methyl-1-propyl isonicotinoate.
43. 2-N,N-Dichloroamino-2-methyl-1-propyl nicotinate N-oxide.
44. 2-N,N-Dichloroamino-2-methyl-1-propyl isonicotinate N-oxide.
45. 2-N,N-Dichloroamino-2-methyl-1-propyl nicotinate hydrochloride.
46. 2-N,N-Dichloroamino-2-methyl-1-propyl nicotinate methylsulfonate.
47. 2-N,N-Dichloroamino-2-methyl-1-propyl nicotinate methylsulfate.
48. 2-N,N-Dichloroamino-2-methyl-1-propyl isonicotinate hydrochloride.
49. 2-N,N-Dichloroamino-2-methyl-1-propyl isonicotinate methylsulfonate.
50. 2-N,N-Dichloroamino-2-methyl-1-propyl isonicotinate methylsulfate.
51. 2-N-Chloroamino-2-methyl-1-propyl methyl ether.
52. 2-N-Chloroamino-2-methyl-1-propyl ethyl ether.
53. 2-N-Chloroamino-2-methyl-1-propyl propyl ether.
54. 2-N-Chloroamino-2-methyl-1-propyl butyl ether.
55. 2-N,N-Dichloroamino-2-methyl-1-propyl methyl ether.
56. 2-N,N-Dichloroamino-2-methyl-1-propyl ethyl ether.
57. 2-N,N-Dichloroamino-2-methyl-1-propyl propyl ether.
58. 2-N,N-Dichloroamino-2-methyl-1-propyl butyl ether.
59. Formaldehyde 2-N-Chloroamino-2-methyl-1-propyl methyl acetal.
60. Formaldehyde 2-N-Chloroamino-2-methyl-1-propyl ethyl acetal.

61. Formaldehyde 2-N,N-dichloroamino-2-methyl-1-propyl methyl acetal.
62. Formaldehyde 2-N,N-dichloroamino-2-methyl-1-propyl ethyl acetal.

The compounds of the present invention can be prepared by simple stepwise procedures as outlined below.

GENERAL REACTION SCHEME (1) The N-Chloramine precursors for the ester derivatives of formula (I) are prepared by (a) N- to O- acyl transfer in the corresponding N-acylated amino alcohol via ethanolic hydrogen chloride[1], Scheme I, (b) hydrolysis of the corresponding $\Delta^2$-1,3-oxazoline in acidic tetrahydrofuran solution containing an equivalent of water based on the $\Delta^2$-1,3-oxazoline[2], Scheme II, or (c) O-acylation of the N-protected amino alcohol with subsequent removal of the N-protective group, Scheme III[3]. All reactions are run at standard temperature and pressure.

[1] A. P. Phillips and R. Baltzly, *J. Amer. Chem. Soc.*, 69, 200 (1947)
[2] P. Allen and J. Ginos, *J. Org. Chem*, 27, 4418 (1962).
[3] James J. Kaminski, Nicolae Bodor and Takeru Higuchi, *J. Pharm. Sci.*, 65, 0000 (1976).

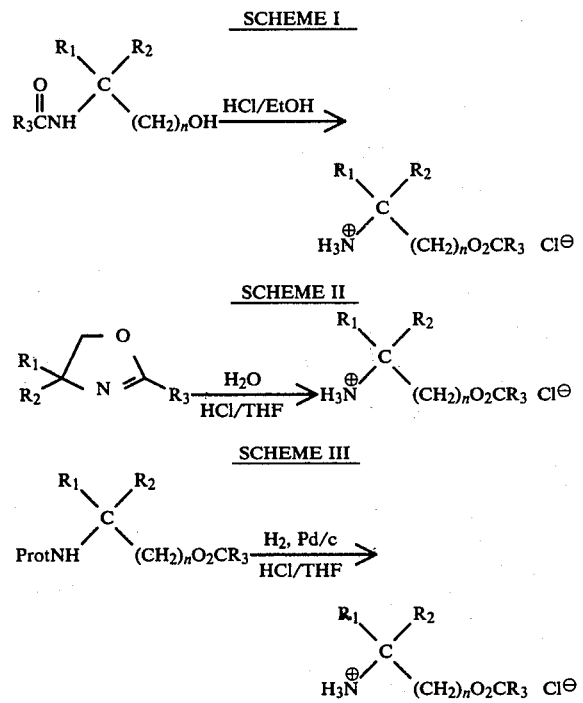

(2) The ether derivative precursors are prepared as follows[4]:
Hodge, *J. Amer. Chem. Soc.*, 70, 2006 (1948).

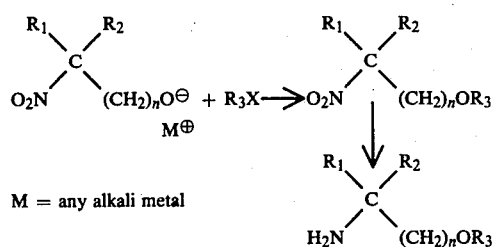

M = any alkali metal (3) The acetal derivative precursor are prepared as follows[4]:
[4] E. B. Hodge, *J. Amer. Chem. Soc.*, 70, 2006 (1948).

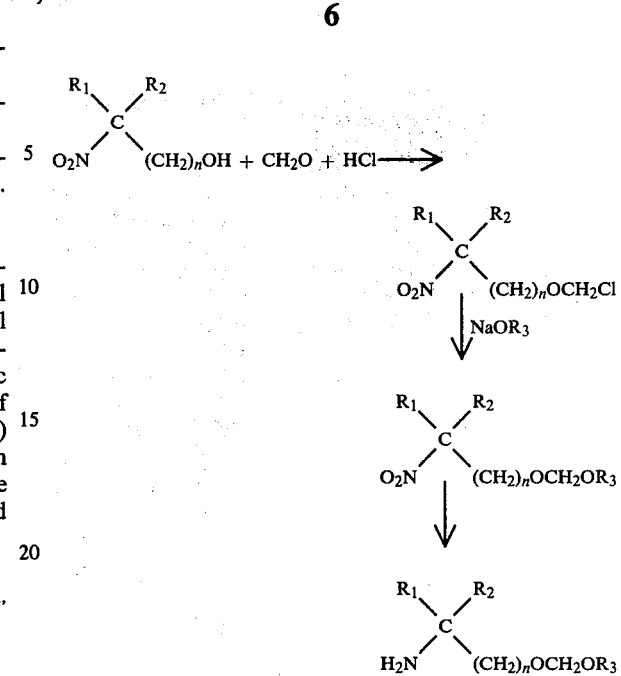

In the above reaction schemes (I) through (III), $R_1$, $R_2$, $R_3$, Y and n are as defined earlier.

Chlorination for all the precursor compounds is easily carried out essentially under the same conditions described above using conventional chlorinating agents, e.g., chlorine, NaOCl, t-BuOCl, N-chlorosuccinimide, etc. The skilled artisan will readily appreciate the fact that the above-mentioned chlorinating agents are only illustrative and nonlimitative as other equivalent chlorinating agents can be employed as well.

Chlorination is normally carried out in a homogeneous solution or suspension at atmospheric pressure and at a temperature of from 0° C. to 25° C., over a period of time, ranging from 0.5 to 5.0 hours.

Chlorination will normally be carried out in a water solvent, except in the case of t-BuOCl. In this situation, anhydrous organic solvents can be employed (e.g., benzene and/or t-Butyl alcohol).

Following chlorination, the chlorinated compound is isolated normally by filtration or extraction in a non-water miscible solvent such as ether, dichloromethane, petroleum ether, or the like. The final compound is purified by conventional methods such as vacuum distillation, sublimation, crystallization, or conventional chromatographic procedures. monochloro Under the above chlorinating conditions, the compounds of formula (I) are normally obtained; however, the monochloro species can also be obtained in certain instances, and namely, when the pH of the reaction mixture is equal to or greater than 9.0.

Without further elaboration, it is believed that one skilled in the art can, using the preceding description, utilize the present invention to its fullest extent. The following preferred specific embodiments are, therefore, to be construed as simply illustrative, and not limitative of the remainder of the specification and claims in any way whatsoever. Reference to temperature, in all instances, refers to Centigrade unless otherwise indicated.

EXAMPLE A

2-Amino-2-methyl-1-propyl acetate hydrochloride (IIIa)

To a dichloromethane solution containing 17.1 g (0.1 mol) carbobenzoxychloride at 0° was added dropwise with stirring 18.4 g (0.2 mol) 2-amino-2-methyl-1-propanol. The reaction mixture was stirred at room temperature overnight and the 2-amino-2-methyl-1-propanol hydrochloride which formed was removed by filtration. Removal of the dichloromethane under reduced pressure afforded a colorless, viscous liquid. Distillation gave 14.9 g (0.07 mol), 70%, 2-carbobenzoxyamino-2-methyl-1-propanol, bp 144°-148° (0.3 mm); ir (neat) 3400, 3020, 2980, 1710, 1510, 1455, 1270, 1070, 730 and 680 cm$^{-1}$; pmr (CDCl$_3$) δ 7.2 (s, 5H), 5.4 (bs, 1H), 4.9 (s, 2H), 4.2 (bs, 1H), 3.4 (s, 2H) and 1.2 (s, 6H) ppm.

To a dichloromethane solution containing 2.52 g (0.011 mol) 2-carbobenzoxyamino-2-methyl-1-propanol and 1.17 g (0.015 mol) acetyl chloride was added dropwise with stirring 1.11 g (0.011 mol) triethylamine. The reaction was stirred at ambient temperature overnight and the dichloromethane was removed under reduced pressure. The triethylamine hydrochloride residue was triturated in anhydrous ether. Following filtration, the ether was removed under reduced pressure to afford 2.38 g (0.009 mol), 82%, crude 2-carbobenzoxyamino-2-methyl-1-propyl acetate as a pale yellow liquid, pmr (CDCl$_3$) δ 7.2 (s, 5H), 5.4 (bs, 1H), 5.0 (s, 2H), 2.0 (s, 3H) and 1.2 (s, 6H) ppm.

2.38 g (0.009 mol) 2-Carbobenzoxyamino-2-methyl-1-propyl acetate was dissolved in 100 ml anhydrous hydrogen chloride in tetrahydrofuran (2 M). 1.0 g of 10% Pd/C was added to the solution and the resulting mixture was hydrogenated under a hydrogen pressure of 50 psi for 2 hours. The catalyst was removed by filtration and thoroughly washed with tetrahydrofuran. Removal of the tetrahydrofuran under reduced pressure gave an off-white solid. Recrystallization from acetone-hexane afforded 1.0 g (0.006 mol), IIIa, as a hygroscopic white solid, mp 146°-149°; pmr (D$_2$O) δ 4.0 (s, 2H), 2.0 (s, 3H) and 1.2 (s, 6H) ppm.

Anal. Calcd for C$_6$H$_{14}$ClNO$_2$·½ H$_2$O: C, 40.79; H, 8.56; N, 7.93. Found: C, 40.31; H, 8.36; N, 8.28.

EXAMPLE B

2-Amino-2-methyl-1-propyl butyrate hydrochloride (IIIb)

To 65 ml of a solution of anhydrous hydrogen chloride in tetrahydrofuran (1 M) containing 1 ml of water was added 7.3 g (0.052 mol) 2-n-propyl-4,4-dimethyl-Δ$^2$-1,3-oxazoline which was prepared using the method of Allen and Ginos (2). The solution was heated under reflux with stirring for 1 hour. The tetrahydrofuran was removed under reduced pressure to afford a semi-solid residue which crystallized at 0° upon the addition of anhydrous ether. The solid was triturated in anhydrous ether overnight and isolated by filtration under a nitrogen atmosphere. After drying in vacuo over calcium sulfate, 7.0 g (0.036 mol), 70%, IIIb, was obtained mp 104°-107°; ir (KBr) 2900, 1740 and 1160 cm$^{-1}$; pmr ((CD$_3$)$_2$CO.D$_2$O) δ 4.2 (s, 2H) 3.8 (bs, 3H), 2.5 (t, 2H), 1.6 (m, 2H), 1.5 (s, 6H) and 1.0 (t, 3H) ppm.

Anal. Calcd for C$_8$H$_{18}$ClNO$_2$: C, 49.10; H, 9.27; N, 7.16. Found: C, 50.01; H, 9.62; N, 7.54.

Using the procedure described for the preparation of IIIb, the following 2-amino-2-methyl-1-propyl carboxylate hydrochlorides were prepared:

EXAMPLE C

2-Amino-2-methyl-1-propyl 2,2-dimethylpropionate hydrochloride (IIIc)

mp 113°-118°; ir (KBr) 3430, 2980, 1735, 1520, 1470, 1270 and 1150 cm$^{-1}$; pmr (D$_2$O) δ 4.10 (s, 2H), 1.4 (s, 6H) and 1.23 (s, 9H) ppm.

Anal. Calcd for C$_9$H$_{20}$ClNO$_2$·H$_2$O: C, 47.46; H, 9.74; N, 6.15. Found: C, 47.86; H, 9.34; N, 6.06.

EXAMPLE D

2-Amino-2-methyl-1-propyl hexanoate hydrochloride (IIId)

mp 100°-101°; (KBr) 2900, 1745 and 1165 cm$^{-1}$; pmr ((CD$_3$)$_2$CO.D$_2$O) δ 4.3 (s, 2H), 3.7 (bs, 3H), 2.5 (t, 2H), 1.2–1.8 (m, 6H), 1.5 (s, 6H) and 0.9 (t, 3H) ppm.

Anal. Calcd for C$_{10}$H$_{22}$ClNO$_2$: C, 53.68; H, 9.91; N, 6.26. Found: C, 53.02; H, 10.21; N, 6.71.

EXAMPLE E

2-Amino-2-methyl-1-propyl octanoate hydrochloride (IIIe)

mp 106°-108°, ir (KBr) 2900, 1750 and 1175 cm$^{-1}$; pmr (D$_2$O) δ 4.2 (s, 2H), 2.5 (t, 2H), 1.5 (s, 6H), 1.2–1.8 (m, 10H) and 0.9 (t, 3H) ppm.

Anal. Calcd for C$_{12}$H$_{26}$ClNO$_2$: C, 57.24; H, 10.41; N, 5.56. Found: C, 57.29; H, 10.52; N, 5.28.

EXAMPLE F

2-Amino-2-methyl-1-propyl nicotinate dihydrochloride (IIIf)

100 g (0.66 mol) Ethyl nicotinate and 88 g (0.99 mol) 2-amino-2-methyl-1-propanol were mixed and heated together under reflux for 2 hours. The excess amino alcohol was removed by distillation, bp 50°-60° (1 mm). The yellow residue was recrystallized from ether-acetone to give 87.3 g (0.45 mol), 68%, N-(1-hydroxy-2-methyl-2-propyl) nicotinamide, mp 91°-93°; ir (KBr) 3385, 3200, 1665, and 1590 cm$^{-1}$; pmr (CDCl$_3$) δ 8.8–7.3 (m, 4H), 6.7 (bs, 1H), 5.0 (s, 1H), 3.7 (s, 2H) and 1.4 (s, 6H) ppm.

Anal. Calcd for C$_{10}$H$_{14}$N$_2$O$_4$: C, 61.90; H, 7.23; N, 14.50. Found: C, 61.87; H, 7.26; N, 14.55.

A suspension of 73.3 g (0.38 mol) N-(1-hydroxy-2-methyl-2-propyl) nicotinamide in 300 ml of anhydrous hydrogen chloride in absolute ethanol (4 M) was heated under reflux for 2 hours. The ethanol was removed under reduced pressure to afford a semi-solid residue which crystallized from acetone on standing. The solid was isolated by filtration under a nitrogen atmosphere and was thoroughly washed with acetone. After drying in vacuo over calcium sulfate, 74 g (0.28 mol), 74%, IIIf, was obtained mp 215°-216° (dec); ir (KBr) 3200-2500, 1735, 1630 and 1600 cm$^{-1}$; pmr (D$_2$O) δ 9.5 (bs, 1H), 9.4–9.1 (m, 2H), 8.3 (q, 1H), 4.6 (s, 2H) and 1.6 (s, 6H) ppm.

Anal. Calcd for C$_{10}$16Cl$_2$N$_2$O$_2$: C, 44.98; H, 5.99; N, 10.49. Found: C, 45.29; H, 6.15; N, 10.06.

EXAMPLE G

2-N,N-Dichloroamino-2-methyl-1-propyl acetate (IVa)

To 50 ml of 0.75 M sodium hypochlorite at 0° was added in portions over 5 minutes 3.19 g (0.019 mol) IIIa.

The reaction mixture was adjusted to ph 4–6 by the addition of 1 M HCl and the suspension was vigorously stirred at 0° for 1 hour. The N-chloramine was extracted into dichloromethane and the extracts combined and dried over anhydrous sodium sulfate. Following filtration, the dichloromethane was removed under reduced pressure to afford a dark yellow liquid. Distillation gave 2.0 g (0.010 mol), 55%, IVa, bp 55°–60° (0.4 mm), ir (neat) 1750, 1230 and 1040 cm$^{-1}$; pmr (CDCl$_3$) δ 4.2 (s, 2H), 2.1 (s, 3H) and 1.4 (s, 6H) ppm.

Anal. Calcd for C$_6$H$_{11}$Cl$_2$NO$_2$: C, 36.02; H, 5.54; N, 7.00. Found: C, 36.40; H, 5.63; N, 6.90.

Using the procedure described for the preparation of IVa, the following 2-N,N-dichloroamino-2-methyl-1-propyl carboxylates were prepared:

EXAMPLE H

2-N,N-Dichloroamino-2-methyl-1-propyl butyrate (IVf)

bp 70°–75° (0.4 mm), ir (neat) 2940, 1740 and 1160 cm$^{-1}$; pmr (CDCl$_3$) δ 4.3 (s, 2H), 2.4 (t, 2H), 1.7 (m, 2H), 1.4 (s, 6H) and 1.0 (t, 3H) ppm.

Anal. Calcd for C$_8$H$_{15}$Cl$_2$NO$_2$: C, 42.12; H, 6.63; N, 6.14. Found: C, 42.30; H, 6.60; N, 6.04.

EXAMPLE I

2-N,N-Dichloroamino-2-methyl-1-propyl 2,2-dimethylproprionate (IVg)

bp 67.5°–68.5° (0.45 mm); ir (neat) 2990, 1740, 1475, 1360, 1270, and 1140 cm$^{-1}$; pmr (CDCl$_3$) δ 4.3 (s, 2H), 1.4 (s, 6H) and 1.2 (s, 9H) ppm.

Anal. Calcd for C$_9$H$_{17}$Cl$_2$NO$_2$: C, 44.64; H, 7.08; N, 5.70. Found: C, 44.51; H, 7.11; N, 5.58.

EXAMPLE J

2-N,N-Dichloroamino-2-methyl-1-propyl hexanoate (IVh)

ir (neat) 2930, 2910, 2840, 1745 and 1155 cm$^{-1}$; pmr (CDCl$_3$) δ 4.2 (s, 2H), 2.3 (t, 2H), 1.2–1.8 (m, 6H), 1.4 (s, 6H) and 0.9 (t, 3H) ppm.

Anal. Calcd for C$_{10}$H$_{19}$Cl$_2$NO$_2$: C, 46.88 H, 7.48; 5.47. Found: C, 46.90; H, 7.49; N, 5.22.

EXAMPLE K

2-N,N-Dichloroamino-2-methyl-1-propyloctanoate (IVi)

ir (neat) 2940, 2860, 1750 and 1150 cm$^{-1}$; pmr (CDCl$_3$) δ 4.2 (s, 2H), 2.3 (t, 2H), 1.1–2.0 (m, 8H), 1.4 (s, 6H) and 0.9 (t, 3H) ppm.

Anal. Calcd for C$_{12}$H$_{23}$Cl$_2$NO$_2$: C, 50.71; H, 8.16; N, 4.93. Found: C, 50.38; H, 8.00; N, 4.70.

EXAMPLE L

2-N-Chloroamino-2-methyl-1-propyl butyrate (IVb)

To 50 ml of 0.75 M sodium hypochlorite at 0° was added in portions over 5 minutes 7.41 g (0.038 mol) IIIb. The suspension was vigorously stirred at 0° for 1 hour. The N-chloramine was extracted into dichloromethane and the extracts were combined and dried over anhydrous sodium sulfate. Following filtration, the dichloromethane was removed under reduced pressure to afford a pale yellow liquid. Distillation gave 5.2 g (0.027 mol) IVb, bp 60°–65° (0.4 mm); ir (neat) 3230, 2930, 1740 and 1160 cm$^{-1}$; pmr (CDCl$_3$) δ 4.2 (s, 2H), 2.4 (t, 2H), 1.7 (m, 2H), 1.4 (s, 6H) and 1.0 (t, 3H) ppm.

Anal. Calcd for C$_8$H$_{16}$ClNO$_2$: C, 49.61; H, 8.33; N, 7.23. Found: C, 49.00; H, 8.47; N, 6.94.

Using the procedure described for the preparation of IVb, the following 2-N-chloroamino-2-methyl-1-propyl carboxylates were prepared:

EXAMPLE M

2-N-Chloroamino-2-methyl-1-propyl 2,2-dimethylproprionate (IVc)

bp 51.6°–63° (0.45 mm); ir (neat) 3280, 2990, 1730, 1475, 1275 and 1140 cm$^{-1}$; pmr (CDCl$_3$) δ 4.6 (bs, 1H), 4.0 (s, 2H), 1.3 (s, 9H) and 1.2 (s, 6H) ppm.

Anal. Calcd for C$_9$H$_{18}$ClNO$_2$: C, 52.04; H, 8.73; N, 6.75. Found: C, 52.04; H, 8.70; N, 6.37.

EXAMPLE N

2-N-Chloroamino-2-methyl-1-propyl hexanoate (IVd)

ir (neat) 3240, 1745 and 1160 cm$^{-1}$; pmr (CDCl$_3$) δ 4.5 (bs, 1H), 4.1 (s, 2H), 2.2 (t, 2H), 1.1–2.0 (m, 6H), 1.3 (s, 6H) and 1.0 (t, 3H) ppm.

Anal. Calcd for C$_{10}$H$_{20}$ClNO$_2$: C, 54.16; H, 9.09; N, 6.32. Found: C, 55.04; H, 9.82; N, 6.70.

EXAMPLE O

2-N-Chloroamino-2-methyl-1-propyl octanoate (IVe)

ir (neat) 3260, 2920, 1740 and 1150 cm$^{-1}$; pmr (CDCl$_3$) δ 4.5 (bs, 1H), 4.1 (s, 2H), 2.4 (t, 2H), 1.1–2.0 (m, 8H), 1.3 (s, 6H) and 0.9 (t, 3H) ppm.

Anal. Calcd for C$_{12}$H$_{24}$ClNO$_2$: C, 57.70; H, 9.68; N, 5.61. Found: C, 57.14; H, 9.72; N, 5.39.

EXAMPLE P

2-N,N-Dichloroamino-2-methyl-1-propyl nicotinate (IVj)

To 58 ml of 0.7 M sodium hypochlorite at 0° was added in portions over 10 minutes 5.32 g (0.02 mol) IIIf. After 0.5 hour at 0°, the pale yellow solid was isolated by filtration and thoroughly washed with cold water. The solid was dried in vacuo over calcium sulfate to give 3.7 g (0.014 mol), 70%, IVj, mp 53°–55°, sublimation at 50° (0.25 mm), ir (KBr) 3020, 3000, 1720, 1580, 1280, 1110, 720 and 670 cm$^{-1}$; pmr (CDCl$_3$) δ 9.3 (s, 1H), 8.9 (d, 1H), 7.6–8.2 (m, 2H), 4.6 (s, 2H) and 1.5 (s, 6H) ppm.

Anal. Calcd for C$_{10}$H$_{12}$Cl$_2$N$_2$O$_2$: C, 45.64; H, 4.60; N, 10.65. Found: C, 45.69; H, 4.71; N, 10.46.

EXAMPLE Q

2-N,N-Dichloroamino-2-methyl-1-propyl nicotinate methylsulfate (IVk)

To 1.3 g (0.005 mol) IVj was added 0.63 g (0.005 mol) dimethyl sulfate. The mixture was heated at 60° under a nitrogen atmosphere for 2.5 hours. The solid mass was triturated with anhydrous ether. The solid was isolated by filtration under a nitrogen atmosphere and thoroughly washed with anhydrous ether. After drying in vacuo over calcium sulfate, 1.87 g (0.0048 mol), 93%, IVk was obtained mp 95°–100° (dec); ir (KBr) 3020, 2980, 1730, 1240, 1200, 1000 and 7.30 cm$^{-1}$; pmr (D$_2$O) δ 9.5 (s, 1H), 9.2 (d, 2H), 8.3 (t, 1H), 4.6 (s, 2H), 3.8 (s, 3H) and 1.6 (s, 6H) ppm; uv (H$_2$O) λmax 303 nm, ε=263 M$^{-1}$cm$^{-1}$.

Anal. Calcd for C$_{12}$H$_{18}$Cl$_2$N$_2$O$_6$S: C, 37.02; H, 4.66; N, 7.20. Found: C, 36.84; H, 4.75; N, 6.92.

EXAMPLE R

2-N,N-Dichloroamino-2-methyl-1-propyl nicotinate methylfluorosulfonate (IVl)

To an ethereal solution containing 1.3 g (0.005 mol) IVj at 0° was added dropwise with stirring 0.57 g (0.005 mol) methylfluorosulfonate in 25 ml anhydrous ether. After stirring at room temperature 4 days, the yellow gummy mass was crystallized by repeated scratching at ambient temperature to a white solid. The solid was triturated with anhydrous ether and isolated by filtration under a nitrogen atmosphere. 1.32 g (0.0035 mol), 70%, IVl was obtained as an extremely hygroscopic white solid, mp (sealed) 112°–118° (dec); pmr (D$_2$0) δ 9.4 (s, 1H), 9.0 (d, 2H), .8.2 (t, 1H), 4.6 (s, 2H), 4.5 (s, 3H) and 1.6 (s, 6H) ppm.

EXAMPLE S

2-Benzoylamino-2-methyl-1-propanol (1)

To a 250 ml dichloromethane solution containing 89 g (1.0 mol) 2-amino-2-methyl-1-propanol at 0° was added dropwise with stirring 70 g (0.5 mol) benzoyl chloride in 250 ml dichloromethane. The reaction mixture was warmed to room temperature and stirred for several hours. The 2-amino-2-methyl-1-propanol hydrochloride was removed from the reaction mixture by filtration and was thoroughly washed with dichloromethane. The filtrate and washings were combined and the dichloromethane removed under reduced pressure to afford 67.55 g (0.35 mol), 70%, 2-benzoylamino-2-methyl-1-propanol as a white solid, mp 80°–82°, sublimation at 75° (0.2 mm); ir (KBr) 1630 (c=o) cm$^{-1}$; pmr (CDCl$_3$) δ 1.50 (s, 6H), 3.67 (s, 2H), 5.27 (bs, 1H), 6.92 (bs, 1H) and 7.1–8.3 (m, 5H) ppm.

Anal. Calcd for C$_{11}$H$_{15}$NO$_2$: C, 68.37; H, 7.82; N, 7.25. Found: C, 68.47; H, 7.96; N, 7.20.

EXAMPLE T

2-Phenyl-4,4-dimethyl-1,3-oxazoline hydrochloride (2)

To 40 ml of freshly distilled thionyl chloride at 0° was added in portions over 15 minutes was stirring 3.86 g (0.02 mol) 2-benzoylamino-2-methyl-1-propanol. The solution was warmed to room temperature and heated under reflux for 2 hours. The thionyl chloride was removed under reduced pressure to afford a yellow oil which crystallized at 0° following the addition of anhydrous ether. The solid was triturated in anhydrous ether overnight and isolated by filtration under a nitrogen atmosphere. After drying in vacuo over calcium sulfate, 2.00 g (0.009 mol), 45%, 2-phenyl-4,4-dimethyl-1,3-oxazoline hydrochloride was obtained as a white solid, mp 149°–151°; ir (KBr) 1640 (c=N) cm$^{-1}$, pmr (D$_2$O) δ 1.60 (s, 6H), 4.70 (s, 2H) and 7.3–8.2 (m, 5H) ppm.

Anal. Calcd for C$_{11}$H$_{14}$ClNO: C, 62.40; H, 6.68; N, 6.62. Found: C, 62.58; H, 6.53; N, 6.44.

EXAMPLE U

2-Amino-2-methyl-1-propyl benzoate hydrochloride (3)

To 8.7 g (0.041 mol) 2-phenyl-4,4-dimethyl-1,3-oxazoline hydrochloride suspended in 120 ml anhydrous hydrogen chloride in tetrahydrofuran (1 M) was added 3.6 ml (0.20 mol) water. The mixture was warmed to cause solution and heated under reflux with stirring for 1 hour. The tetrahydrofuran was removed under reduced pressure to afford a nearly colorless oil which crystallized at 0° following the addition of anhydrous ether. The solid was triturated with anhydrous ether overnight and isolated by filtration under a nitrogen atmosphere. After drying in vacuo over calcium sulfate, 6.9 g (0.30 mol), 73%, 2-amino-2-methyl-1-propyl benzoate hydrochloride was obtained as a white solid, mp 225°–228° (dec.) acetone:hexane, ir (KBr) 1725 (c=o) cm$^{-1}$, pmr (D$_2$O) δ 1.50 (s, 6H), 4.4 (s, 2H) and 7.0–8.3 (m, 5H) ppm.

Anal. Calcd for C$_{11}$H$_{16}$ClNO$_2$: C, 57.51; H, 7.02; N, 6.10. Found: C, 57.73; H, 6.77; N, 6.05.

EXAMPLE V

MINIMAL INHIBITORY CONCENTRATION OF 2-AMINO-2-METHYL-1-PROPYL CARBOXYLATES

| Compound | S. aureus | S. pyogenes | E. coli | K. pneumoniae | P. aeruginosa | A. niger | C. albicans | T. mentagrophytes |
|---|---|---|---|---|---|---|---|---|
| IV a  | >62.5[b] | 62.5  | >62.5 | >62.5 | 62.5  | >62.5 | >62.5 | 62.5  |
| III b | >62.5   | >62.5 | >62.5 | >62.5 | >62.5 | >62.5 | >62.5 | >62.5 |
| IV b  | >62.5   | 62.5  | >62.5 | >62.5 | >62.5 | >62.5 | >62.5 | >62.5 |
| IV f  | >62.5   | 62.5  | >62.5 | >62.5 | 62.5  | >62.5 | >62.5 | >62.5 |
| IV c  | >250    | >125  | >250  | >250  | >250  | >250  | >250  | >250  |
| IV g  | 250     | 250   | >125  | >125  | 250   | >125  | >125  | >125  |
| III d | >62.5   | 62.5  | >62.5 | >62.5 | 62.5  | >62.5 | >62.5 | >62.5 |
| IV d  | >62.5   | >62.5 | >62.5 | >62.5 | >62.5 | >62.5 | >62.5 | >62.5 |
| IV h  | >62.5   | 62.5  | >62.5 | >62.5 | >62.5 | >62.5 | >62.5 | 62.5  |
| III e | >62.5   | >62.5 | >62.5 | >62.5 | >62.5 | >62.5 | >62.5 | >62.5 |
| IV e  | >62.5   | >62.5 | >62.5 | >62.5 | >62.5 | >62.5 | >62.5 | >62.5 |
| IV i  | 62.5    | 62.5  | >62.5 | >62.5 | >62.5 | >62.5 | >62.5 | 62.5  |
| IV k  | >250    | >250  | >250  | >250  | >250  | 125   | >250  | 125   |

[a]Minimal inhibitory concentration expressed in parts per million (ppm) of compound.
[b]Greater than (>) indicates that the solvent content in thedilution sequence inhibited the test organism at the higher concentrations.

EXAMPLE W

CONTACT GERMICIDAL EFFICIENCY OF 2-AMINO-2-METHYL-1-PHROPYL CARBOXYLATES

| Compound | Concentration[b] PPM, PPMCl$^-$ | | S. ureus | S. pyogeners | E. coli | S. typhimurium | B. Subtilis |
|---|---|---|---|---|---|---|---|
| | PPM | PPMCl$^+$ | | | | | |
| IV a  | 1292, | 458 | 5   | 2.5 | 0.5 | 2.5 | 2.5 |
| III b | 1070, |     | >60 | >60 | >60 | >60 | >60 |
| IV b  | 2078, | 380 | 2.5 | 0.5 | 0.5 | 2.5 | 2.5 |

EXAMPLE W-continued

CONTACT GERMICIDAL EFFICIENCY OF 2-AMINO-2-METHYL-1-PHROPYL CARBOXYLATES

| Compound | Concentration[b] PPM | PPMCl− | S. ureus | S. pyogeners | Sterilization Time[a] (Minutes) E. coli | S. typhimurium | B. Subtilis |
|---|---|---|---|---|---|---|---|
| IV f | 979, | 304 | 2.5 | 0.5 | 0.5 | 2.5 | 2.5 |
| IV c | 1886, | 323 | 5 | 0.5 | 0.5 | 2.5 | 2.5 |
| IV g | 409, | 120 | 5 | 2.5 | 2.5 | 5 | 2.5 |
| III d | 1037, | | >60 | >60 | >60 | >60 | >60 |
| IV d | 1319, | 211 | 2.5 | 0.5 | 2.5 | 5 | 2.5 |
| IV h | 95, | 26 | 10 | 2.5 | 10 | 10 | 2.5 |
| III e | 1040, | | >60 | 30 | 15 | 30 | 5 |
| IV e | 300, | 43 | 10 | 2.5 | 5 | 10 | 0.5 |
| IV i | 85, | 21 | 15 | 5 | 10 | 10 | 2.5 |

[a]Time intervals screened 0.5, 2.5, 5, 10, 15, 30, 45 and 60 minutes.
[b]Solubility in 30% methanol: 0.1 M sodium dihydrogen phosphate, pH 7.0.

EXAMPLE X

CONTACT GERMICIDAL EFFICIENCY OF N-CHLORAMINES AS A FUNCTION OF THE SOLUTION pH IN THE ABSENCE OF HORSE SERUM

| Compound | Concentration PPM | PPMCl+ | pH | S. epidermidis | S. aureus | Sterilization Time[a] (Minutes) E. coli | K. pheumoniae | P. aeruginosa | B. bronchiseptica |
|---|---|---|---|---|---|---|---|---|---|
| | 404 | 69 | 4.6 | 0.5 | 1 | 0.5 | 0.5 | 0.5 | 0.5 |
| IV c | 1886 | 323 | 7.0 | 3 | 4 | 0.5 | 2 | 1 | 1 |
| | 1704 | 292 | 9.3 | 4 | 3 | 1 | 2 | 1 | 1 |
| | 489 | 143 | 4.6 | 0.5 | 2 | 0.5 | 0.5 | 0.5 | 1 |
| IV g | 409 | 120 | 7.0 | 2 | 4 | 1 | 3 | 0.5 | 2 |
| | 319 | 94 | 9.3 | 2 | 2 | 1 | 2 | 0.5 | 2 |

[a]Time invervals screened 0.5, 1, 2, 3, 4 and 5 minutes.

EXAMPLE Y

CONTACT GERMICIDAL EFFICIENCY OF N-CHLORAMINES AS A FUNCTION OF THE SOLUTION pH IN THE PRESENCE OF HORSE SERUM

| Compound | Concentration PPM | PPMCl+ | pH | S. epidermidis | S. aureus | Sterilization Time[a] (Minutes) E. coli | K. pneumoniae | P. aeruginosa | B. bronchiseptica |
|---|---|---|---|---|---|---|---|---|---|
| IV c | 468 | 80 | 4.6 | >10 | >10 | >10 | >10 | >10 | >10 |

[a]Time intervals screened 0.5, 1, 2, 3, 4, 5, 6, 7, 8, 9 and 10 minutes unless otherwise noted.

EXAMPLE Z

CONTACT GERMICIDAL EFFICIENCY OF N-CHLORAMINES CONTAINING A POSITIVE CHARGE

| Compound | Concentration | | | S. epidermidis | S. aureus | Sterilization Time (Minutes) E. coli | K. pneumoniae | P. aeruginosa | B. bronchiseptica |
|---|---|---|---|---|---|---|---|---|---|
| In the Absence of Horse Serum:[a] | | | | | | | | | |
| | PPM | PPMCl+ | pH | | | | | | |
| IV j | 79 | 21 | 4.6 | 3 | 5 | 2 | 1 | 2 | 4 |
| IV k | 5800 | 1057 | 4.6 | 4 | 5 | 1 | 2 | 2 | 1 |
| IV l | 1112 | 209 | 4.6 | 3 | 5 | 1 | 5 | 3 | 5 |
| In the Presence of Horse Serum:[b] | | | | | | | | | |
| | PPM | PPMCl+ | pH | | | | | | |
| IV k | 5800 | 1057 | 4.6 | 4 | 6 | 0.5 | 2 | 2 | 2 |

[a]Time intervals screened 0.5, 1, 2, 3, 4, and 5 minutes.
[b]Time intervals screened 0.5, 1, 2, 3, 4, 5, 6, 7, 8, 9 and 10 minutes.

THE ANTIBACTERIAL SCREEN—EXAMPLE V

Test Solution

Immediately preceding the screen, the compound is weighed and diluted with a buffer or other solvent to give the final concentration desired. The buffer or solvent chosen depends on the conditions of the screen and could be one of the following: 0.1 M NaOAc, pH 4.6; 0.1 M NaH$_2$PO$_4$, pH 7.0; 0.1 M Na$_2$B$_4$O$_7$, pH 8.8; 35% methanol in one of the aforementioned buffers; 10% Triton X 100 in buffer, etc.

The positive chlorine concentration of the test solution is then determined iodometrically.

Cultures and Media

Media used for the Screen are Nutrient Broth, BBL# 11479 and Nutrient Agar, BBL# 11472 prepared according to label directions. The broth is dispensed in 75 ml amounts to flasks for overnight cultures and in 5 ml amounts to culture tubes for subculturing during the Screen. Agar plates are prepared as usual.

Overnight cultures are prepared by inoculating from stock cultures into the 75 ml flasks of nutrient broth and incubating for 15 hours at 37° C.

The organisms ordinarily screened are:

| | |
|---|---|
| *Streptococcus pyogenes* | ATCC# 19615 |
| *Aspergillus niger* | ATCC# 6538 |
| *Candida albicans* | ATCC# 10231 |

| | |
|---|---|
| Pseudomonas aeruginosa | ATCC# 9027 |
| Klebsiella pneumoniae | ATCC# 10031 |
| Escherichia coli | ATCC# 10536 |
| Trichophyton mentagrophytes | ATCC# 9129 |

The organisms are maintained as stock cultures on nutrient agar at 4° C. They are transferred and checked for purity monthly.

Procedure

The iodometrically characterized test solution is dispensed in 5 ml amounts to seven small stoppered flasks. The organisms are screened one at a time as follows:

A 0.2 ml portion of the overnight culture is inoculated into 5 ml of 0.9% NaCl for use in controls. A 0.2 ml portion of the overnight culture is inoculated into a flask containing 5 ml of the test solution, an automatic timer is simultaneously triggered and the solution mixed. At time intervals of 30 seconds, 1, 2, 3, 4, 5, 6, 7, 8, 9, and 10 minutes a loopful of the inoculated solution is subcultured into 5 ml of sterile nutrient broth and mixed by a Vortex Genie Mixer, the high dilution serving to stop the action of the compound. At the end of the ten minute screen, the entire procedure is repeated for each of the remaining six organisms. All of the subculture tubes are incubated at 37° C. and checked for signs of growth by turbidity at 24 hr., 48 hr., 3, 5, and 7 days. The earliest subculture time at which no growth is present in the subculture tube is considered the endpoint and is recorded as that time, e.g., 7 minutes.

Controls

Viability of Stock Cultures 0.2 ml of the stock culture is transferred to 5 ml of saline (to simulate 0.2 ml in 5 ml test solution). A loopful of this mixture is subcultured to 5 ml of nutrient broth as in the Screen and incubated at 37° C. for 24 hr. Turbidity indicates that the organism would grow when not in the presence of the test solution.

Purity of Stock Cultures

A loopful of the stock culture in saline is streaked onto nutrient agar to insure the purity and identity of each culture (the cultures are also checked biochemically each month for this purpose).

Dilution of the Test Solution

A loopful of the test solution is diluted in a 5 ml amount of nutrient broth. A loopful of the organism in saline is inoculated into this tube. Turbidity after 24 hr. at 37° C. indicates that the dilution of the test solution in the nutrient broth subculture during the Screen is great enough to stop the action of the compound.

Purity of Organisms in Test Solution

At the end of the Screen a loopful of the organism-test solution mixture is streaked onto nutrient agar to insure that contamination has not occurred during the 10 minute period of the Screen. Often there is no growth at this time if the compound has effectively inhibited all the organisms.

Lack of Bacteriacidal Activity of Buffers and Other Solvents

Before a buffer or other solvent is used as the diluent, it is screened against the organisms Staphylococcus aureus, ATCC# 6538 and Escherichia coli ATCC# 10536 (the 'strongest' and 'weakest' of the organisms) to insure that the buffer or solvent has no antibacterial activity in itself. Subculture times of 10, 20 and 30 minutes are used. Incubation conditions are the same.

Variations

Serum as a Denaturant of the Compound

The test solution is prepared and characterized as above but is made up at twice the concentration desired. The solution is diluted 1:1 with Rehydrated Tissue Culture Dessicated Horse Serum, Difco #5357-72 and dispensed in a 5 ml amount to a small flask. The mixture is incubated at Room Temperature for 30 minutes to allow denaturation of the compound by the serum and then screened as above.

The 5 ml mixture of serum and test solution are prepared in sequence to allow as close to 30 minutes as possible before the beginning of the screen of each organism.

Variation of Conditions

Each new compound is generally screened several times at different concentrations, different pH's, in different solvents and at each of those conditions with and without serum as a denaturant.

THE ANTIBACTERIAL SCREEN—EXAMPLES W–Z (Autotiter IV)

Program I. In vitro antimicrobial screen.

1. Methodologies (a) Compounds. All compounds to be screened are weighed (approx. 10 mg) on the day preceding the test date. Each compound is solubilized on the day of assay in appropriate solvent and diluted automatically in the Autotiter IV with distilled water (buffer can be employed here also).

(b) Organisms.

Bacteria: Staphylococcus aureas Smith (or 209), Escherichia coli AB 1932-1, 1100/B22 and Vogel, Streptococcus pyrogenes C203, Salmonella typhimurium 14028, Bacillus subtilis 6051-1, Klebsiella pneumoniae 10031, Pseudomonas aeruginosa 9027, Bordetella bronchiseptica 4617 and Staphylococcus epidermidis 12228.

(c) Inocula. Prior to utilization in the Autotiter IV, all bacteria are cultured for 18–20 hr. (37° C.) in tryptose phosphate broth (TP), except, S. pyrogenes C203, which is cultured in Brain Heart Infusion broth plus 10% normal horse serum. Immediately prior to testing, each culture is adjusted to an optical density of 0.10 (650 nm), employing a Bausch & Lomb Spectronic 20, and diluted subsequently into double strength medium to approximately $2 \times 10^5$ viable organisms per ml.

(d) Program for Routine Testing.

1. An automated injector system dispenses 0.05 ml of diluent (sterile H$_2$O or buffer) to all cups of the autotiter trays from rows 2 through 7.

2. The loops (for sequential dilutions of the compounds are moistened by immersion into 70% ethyl alcohol. After removal of excess alcohol by blotting, the loops are moved to the first row of cups in the autotray containing 0.10 ml of the compound to be diluted and tested (usually, this initial concentration is 500 to 1000 mcg/ml, but can be varied upward or downward). The loops are lowered and sequentially transfer the diluted solutions of the compound through row 7.

Immediately after each dilution is made, each cup is automatically inoculated with 0.05 ml of the appropriate test organism. This inoculation derives from a second injector system containing the organism in double-strength medium. The total operation consists of the automatic dilution of a single compound in each of 8 rows of the Autotiter try.

After these operations, we reverse the tray and a second compound is diluted over the other one-half of the tray and inoculated, subsequently, with 8 organisms. Thus, for each Autotiter Tray, two compounds are screened against 8 different organisms at dilutions ranging from 1:2 to 1:128.

(e) Incubation. The inoculated Autotiter trays are incubated at 37° C. for 18–20 hr. At the end of this period, each tray is examined for the presence or absence of growth (turbidity). The lowest concentration of the compound inhibiting growth is recorded as the minimal inhibitory concentration (MIC).

Yeast and fungi are tested in the same manner except that (i) Maltose Peptone broth is employed and (ii) the Autotiter trays are sealed with plastic tape during the incubation period (25° C./5 days) to prevent evaporation.

The compounds of the present invention find wide application as antibacterial agents per se, in aqueous solution, or in such preparations as mouthwashes, shampoos, soaps, cosmetic bases and the like. Such formulations can be prepared in accordance with any of the described procedures disclosed in "REMINGTON's PHARMACEUTICAL SCIENCES" (Fourteenth Edition) 1970. Naturally, the antibacterial effective amount required for a compound of this invention will vary with the microorganism in question.

From the foregoing description, one skilled in the art can easily ascertain the essential characteristics of this invention, and without departing from the spirit and scope thereof, can make various changes and modifications of the invention to adapt it to various usages and conditions. As such, such changes and modifications are properly, equitably, and intended to be, within the full range of equivalence of the following claims.

What we claim is:

1. A compound having the formula:

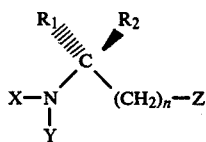

(I)

wherein

X and Y each represent a member which may be the same or different selected from the group consisting of H and Cl with the proviso that X and Y cannot represent H simultaneously;

$R_1$ and $R_2$ each represent a member which may be the same or different selected from the group consisting of n- or branched alkyl of from 1 to 20 carbon atoms;

n represents an integer of 1 to 8; and

Z is $-OOCR_3$, wherein $R_3$ is n- or branched alkyl of 1 to 6 carbon atoms.

2. The compound of claim 1, wherein both $R_1$ and $R_2$ have from 1 to 5 carbon atoms.

3. The compound of claim 1:
2-N-Chloroamino-2-methyl-1-propyl acetate.

4. The compound of claim 1:
2-N-Chloroamino-2-methyl-1-propyl propionate.

5. The compound of claim 1:
2-N-Chloroamino-2-methyl-1-propyl butyrate.

6. The compound of claim 1:
2-N-Chloroamino-2-methyl-1-propyl isobutyrate.

7. The compound of claim 1:
2-N-Chloroamino-2-methyl-1-propyl valerate.

8. The compound of claim 1:
2-N-Chloroamino-2-methyl-1-propyl isovalerate.

9. The compound of claim 1:
2-N-Chloroamino-2-methyl-1-propyl hexanoate.

10. The compound of claim 1:
2-N-Chloroamino-2-methyl-1-propyl 2,2-dimethylpropionate.

11. The compound of claim 1:
2-N,N-Dichloroamino-2-methyl-1-propyl acetate.

12. The compound of claim 1:
2-N,N-Dichloroamino-2-methyl-1-propyl propionate.

13. The compound of claim 1:
2-N,N-Dichloroamino-2-methyl-1-propyl butyrate.

14. The compound of claim 1:
2-N,N-Dichloroamino-2-methyl-1-propyl isobutyrate.

15. The compound of claim 1:
2-N,N-Dichloroamino-2-methyl-1-propyl valerate.

16. The compound of claim 1:
2-N,N-Dichloroamino-2-methyl-1-propyl isovalerate.

17. The compound of claim 1:
2-N,N-Dichloroamino-2-methyl-1-propyl hexanoate.

18. The compound of claim 1:
2-N,N-Dichloroamino-2-methyl-1-propyl 2,2-dimethyl propionate.

* * * * *